(12) United States Patent
Sugita et al.

(10) Patent No.: US 8,348,902 B2
(45) Date of Patent: Jan. 8, 2013

(54) SYRINGE HOLDER AND INJECTION DEVICE

(75) Inventors: Kouichi Sugita, Osaka (JP); Hiroshi Matsumoto, Hyogo (JP)

(73) Assignee: JCR Pharmaceuticals Co., Ltd., Hygo (JP)

( * ) Notice: Subject to any disclaimer, the term of this patent is extended or adjusted under 35 U.S.C. 154(b) by 618 days.

(21) Appl. No.: 11/586,519

(22) Filed: Oct. 26, 2006

(65) Prior Publication Data
US 2007/0100294 A1 May 3, 2007

(30) Foreign Application Priority Data
Oct. 27, 2005 (JP) .................. 2005-313204

(51) Int. Cl.
*A61M 5/32* (2006.01)
(52) U.S. Cl. ....................................... 604/192
(58) Field of Classification Search .......... 604/192, 604/187, 110, 111; 128/919
See application file for complete search history.

(56) References Cited

U.S. PATENT DOCUMENTS

| | | | |
|---|---|---|---|
| 3,958,570 A | | 5/1976 | Vogelman et al. |
| 4,367,738 A | * | 1/1983 | Legendre et al. ............. 604/110 |
| 4,540,405 A | | 9/1985 | Miller et al. |
| 4,723,945 A | | 2/1988 | Theiling |
| 5,876,379 A | | 3/1999 | Beauvais et al. |
| 6,033,387 A | | 3/2000 | Brunel |
| 6,164,044 A | | 12/2000 | Porfano et al. |
| 6,250,052 B1 | | 6/2001 | Porfano et al. |
| 6,692,463 B1 | * | 2/2004 | Marteau et al. ............... 604/110 |
| 2004/0030294 A1 | * | 2/2004 | Mahurkar ..................... 604/192 |
| 2005/0192534 A1 | * | 9/2005 | Wolbring et al. ............. 604/111 |

FOREIGN PATENT DOCUMENTS

EP    0740942 A1    11/1996
(Continued)

OTHER PUBLICATIONS

Maeda Sangyo KK, "Preparing device for multi-chamber syringe and injection device," Patent Abstract of Japan, Publication Date: Mar. 23, 1999; English Abstract of JP-11-076404.

(Continued)

*Primary Examiner* — Nicholas Lucchesi
*Assistant Examiner* — Weng Lee
(74) *Attorney, Agent, or Firm* — Millen, White, Zelano & Branigan, P.C.

(57) ABSTRACT

An injection device adapted to the luer lock system and a syringe holder for making it is disclosed. The syringe holder for holding an inserted syringe, with a cap attached to the male luer at the tip, comprises a cylindrical barrel portion having an open distal end and an open proximal end, and a finger rest around the outer surface of the barrel portion at a position relatively closer to the proximal end, wherein a stopper means is provided at the inner surface of the barrel portion at the distal end thereof, the stopper means being designed to abut on the outer edge of the distal end of the syringe, and wherein a female-threaded sleeve extends forwardly from the distal end of the barrel portion, which is designed to surround the tip of the syringe and the cap, and wherein a proximal end cap is provided, at the proximal end of the barrel portion, which is designed to abut on the outer edge of the proximal end of the syringe, and has a bore to pass the piston rod through.

12 Claims, 3 Drawing Sheets

FOREIGN PATENT DOCUMENTS

| | | |
|---|---|---|
| EP | 0845275 A | 6/1998 |
| EP | 845275 A2 * | 6/1998 |
| JP | 156783 B4 | 12/1989 |
| JP | 10155905 | 6/1998 |
| JP | 11-76404 | 3/1999 |
| JP | 2005 176926 | 7/2005 |
| WO | WO-94 13339 | 6/1994 |
| WO | WO 02/098494 A | 12/2002 |

OTHER PUBLICATIONS

Nihon Medi Physics Co Ltd., "Syringe device," Patent Abstracts of Japan, Publication Date: Jul. 7, 2005; English Abstract of JP-2005 176926.

* cited by examiner

SYRINGE HOLDER AND INJECTION DEVICE

FIELD OF THE INVENTION

The present invention relates to a syringe holder designed to be used to build, with a syringe having a simple luer-type tip, an injection device which is adapted to the luer lock system, as well as an injection device comprising that holder and a syringe which is held by the holder.

BACKGROUND OF THE INVENTION

For connecting a syringe and a counterpart connection device such as a needle or a connection port of infusion tubing or an infusion pump, or the like, the simple luer fitting system is generally employed, which is achieved by fitting of a male luer provided at the tip of the former to a female luer provided in the latter. Further, in addition to the simple luer system, another type of system (luer lock system) has been employed for connection to, e.g., infusion tubing, where a female luer is screw-cramped around itself for the purpose of securely fix the fitting to prevent its easy displacement by external forces. As syringes that are also adapted to the luer lock system, there are known such ones that are equipped with a female-threaded plastic sleeve at their tips surrounding the male luers (see Patent Document 1, FIG. 2). This configuration has made it possible to provide, using a single type of syringes, two types of products i.e., one type adapted only to the simple luer system and the other adapted to the luer lock system.

FIG. 1 illustrates this type of luer lock syringe that is commonly used, which is equipped at its tips with the above type of female-threaded sleeve 2 (shown in a cross sectional view) and a cap 3. In the figure, numeral 4 indicates a gasket which is pressed from behind to advance within the syringe 1, numeral 5 an injectable liquid enclosed in the syringe 1. FIG. 2 illustrates an enlarged view of the tip portion of the above-mentioned luer lock syringe. As seen in FIG. 2, the sleeve 2 is attached by fitting it around a squeezed portion 6 at the root of the male luer at the tip of the syringe 1.

In the case of this conventional luer lock syringe, since the sleeve 2 is to be attached by fitting around the squeezed portion 6 at the root of the male luer of the syringe 1, attachment of the sleeve 2 is blocked if the cap 3 is already fitted on the male luer at the tip of the syringe 1. On the other hand, in order to fill the syringe 1 with an injectable liquid, the cap 3 must be fitted beforehand to seal the tip of the syringe. Consequently, the sleeve 2 must be attached to the tip of the syringe 1 before the cap 3 is fitted at the tip of the syringe, therefore, necessarily before the syringe 1 is filled with the injectable liquid.

Since injectable preparations must be supplied under a sterile condition, it is necessary that the syringe 1, which must be sterilized, must be filled with an injectable liquid in a sterile environment (in an aseptic room). The syringe 1, the cap 3 and the gasket 4, therefore, must be sterilized in advance and then brought over into an aseptic room while keeping them in a sterile condition. As aforementioned, since a conventional luer lock syringe is filled with an injectable liquid, with its sleeve 2 already attached to it, the sleeve 2 also must be sterilized in advance and, while being kept sterile, brought over into a aseptic room. In this circumstance, before filling a luer lock syringe with the injectable liquid, components are conventionally brought over into the aseptic room following either of the two procedures mentioned below.

(1) A syringe having a female-threaded sleeve attached to it, a cap (either separately or as attached to the syringe) and a gasket are brought in the aseptic room for filling with an injectable liquid.

(2) A syringe, a female-threaded sleeve, a cap and a gasket are brought in the aseptic room for filling with an injectable liquid, all as separate components.

According to the above procedure (1), a syringe must be sterilized in advance, with a female-threaded sleeve (or further a cap) attached to it, before they are brought in. Though a syringe itself may be subjected to a convenient procedure of hot air sterilization if it is made of glass, a plastic female-threaded sleeve attached to it cannot withstand it. Therefore, they are sterilized by the process of gas sterilization, autoclave sterilization, gamma ray sterilization or electron beam sterilization, and the like. Whatever the method for sterilization is employed, attachment of the sleeve (or further the cap) to the tip of the syringe before sterilization must be done in an environment that would not cause contamination with microbes, and this leads to substantial amount of costs.

According to the above procedure (2), although it is an advantage that pre-sterilization assembling of the components is not necessary, and therefore each of the components may be sterilized separately, it needs a sterility control, which is costly, for an increased number of sterilized components is to be brought over into the aseptic room, while they all are kept sterile. In addition, since a process of fitting a female-threaded sleeve around the tip of the syringe in the aseptic room is placed prior to filling with the injectable liquid, it is necessary to sterilize and assemble machines and their parts used for this purpose. This makes it difficult to improve the production efficiency as a whole. Further, fracture of the male luer at its root and damage to the sleeve are apt to happen when the sleeve is being attached. And, when such a problem or improper fitting of the both parts does happen, cleaning of the line and readjusting of the machines are extremely difficult to perform in the special circumstance in the aseptic room, thus greatly lowering the productivity.

Another injection device is further known as providing an injection device adapted to the luer lock system through combination of a syringe having a simple luer-type tip and a certain additional part, i.e., an injection device comprising a cylindrical injection device body (i.e., holder) having at its distal end a threaded cylinder portion, a cylindrical ampoule inserted in it, with the tip of the ampoule is fixed by fitting the conical portion for engagement at the root of the male luer in a conical bore made in the injection device body, and a removable securing sleeve which secures the proximal end portion of the ampoule (see Patent Document 2). However, even with this injection device, it is impossible to insert the syringe into the injection device body when a cap is attached to the tip of the syringe, for the holder (therefore the threaded cylindrical portion) and the ampoule (i.e., syringe) are secured around the root of the male luer. Therefore, the process of filling with the injectable liquid is possible only after the syringe is inserted in the holder and the cap is attached to the male luer positioned at the distal end of the holder. Thus, there are the same problems as mentioned, also with regard to above procedures (1) and (2).

As a holder to make an injectable device adapted to the luer lock system from a simple luer-tip syringe, there is known a holder which, utilizing a syringe having a finger rest projection at its proximal end, secures the projection by sandwiching it at the proximal end of the holder (see Patent Document 3). However, with conventionally used syringes having a finger rest projection, as there are of many types and sizes in the length of the syringe barrel and in the thickness of the projection, use of such a projection as an element for holding the syringe would cause unstable holding and also make the position of the tip of the syringe likely to vary in the holder.

As aforementioned, with conventional luer lock syringes, it is difficult to improve the efficiency of production processes from sterilization of their parts to filling with an injectable liquid, thus presenting factors that increase the production cost as a whole.

Besides the above-mentioned problems, there are such types, among counterpart connector devices to which a luer-type tip syringe is to be connected, that are not adapted to the luer lock system and interfere with the female-threaded sleeve, thereby preventing connection from being achieved. When connection is to be made between a syringe and such types of devices, it is a routine practice that the cap is removed from the male luer and then the female-threaded sleeve is ripped by force, using pliers or the like, from the tip of the syringe. As a result, there have arisen frequent problems such as fracture of the male luer and contamination of the tip. With this regard, the injection device or the holder described in the aforementioned Patent Document 2 or 3 have further problems that, since the threaded potion at their distal end cannot even be removed and, further, they do not allow the ampoule (i.e., syringe) to be pulled out from the body (i.e., holder) of the injection device without avoiding dropping off of the cap, they cannot be used with such a counterpart connector device that can only be connected to an exposed type male luer of the simple luer system.

[Patent Document 1] U.S. Pat. No. 6,250,052

[Patent Document 2] Japanese Patent Publication H1-56783

[Patent Document 3] Japanese Patent Application Publication H10-155905

SUMMARY OF THE INVENTION

Against the above-mentioned background, a first objective of the present invention is to provide a syringe holder which is adapted to the luer lock system and yet which allows improvement of the troublesome processes in the production of conventional luer lock syringes from the sterilization of the components to the filling with an injectable liquid, thereby increasing the production efficiency and reducing costs, as well as to provide an injection device comprising such a holder and a syringe that is held by it.

In addition, a second objective of the present invention is to provide a syringe holder which is adapted to the luer lock system and yet which allows easy connection to a female luer of a device that is not adapted to the luer lock system, as well as to provide an injection device comprising a syringe held by such a syringe holder.

As a result of studies addressed to the above-mentioned objectives, the present inventors have found that the first objective can be achieved by, instead of a conventional female-threaded sleeve attached around the root of the male luer, a syringe holder including a generally cylindrical barrel into which a syringe can be inserted, with a cap kept attached to its tip, and integrally having, at the distal end of the barrel, a female-threaded sleeve adapted to the luer lock system. The present inventors further found that such a syringe holder can be made into a configuration that allows removal of a distal portion of it even after a syringe is inserted, so that connection can be made to a female luer of a connector device that is not adapted to the luer lock system, without risks of fracture or contamination of the male luer. The present invention has been accomplished by further studies based on these findings. Thus, the present invention provides what follows.

1. A syringe holder for holding an inserted cylindrical syringe, with a cap attached to a male luer provided at the distal end thereof, comprising a generally cylindrical barrel portion having an open distal end and an open proximal end, and a finger rest projecting in the lateral direction from the outer surface of the barrel portion at a position relatively closer to the proximal end of the barrel portion, wherein a stopper means is provided at the inner surface of the barrel portion at the distal end thereof, the stopper means being designed to abut on the outer edge of the distal end of the syringe to block forward movement of the syringe, wherein a female-threaded sleeve is provided which extends forwardly from the distal end of the barrel portion, the female-threaded sleeve being provided with a thread designed to surround the male luer provided at the distal end of the syringe and the cap attached to the male luer, and wherein a proximal end cap is provided, at the proximal end of the barrel portion, the proximal end cap being designed to cover the proximal end of the barrel portion and to abut on the outer edge of the proximal end of the syringe to block backward movement of the syringe, and the proximal end cap having a bore through which to pass a piston rod that is to be connected to a gasket in the syringe.

2. The syringe holder as defined in 1 above, wherein the stopper means is of a shape and dimensions that do not block the passage of the cap upon insertion of the syringe into the syringe holder.

3. The syringe holder as defined in 1 or 2 above, wherein the stopper means consists of an inward upthrust from the inner surface of the barrel portion.

4. The syringe holder as defined in one of 1 to 3 above, wherein the stopper means does not intrude into the inside of a cylindrical surface defined by the top of the thread of the female-threaded sleeve.

5. The syringe holder as defined in one of 1 to 4 above, wherein the proximal end cap is attached to the proximal end of the barrel portion by screw engagement between the outer surface of the barrel portion at or close to the proximal end thereof and the inner surface of the proximal end cap.

6. The syringe holder as defined in one of 1 to 5 above, wherein the barrel portion consists of a distal portion and a proximal portion which are separably connected with each other at a site forward of the finger rest.

7. The syringe holder as defined in 6 above, wherein the connection is made in a manner that rear part of the distal portion covers the front part of the proximal portion.

8. The syringe holder as defined in 6 above, wherein the connection is made by screw engagement between a female screw formed on the inner surface of the rear part of the distal portion and a male screw formed on the outer surface of the front part of the proximal portion.

9. An injection device comprising a cylindrical syringe having a gasket inserted therewithin and a cap attached to a male luer provided at the distal end thereof, the syringe holder as defined in one of 1 to 8 above holding the syringe therein, and a piston rod passing through the bore in the proximal end cap for the syringe holder and connected, at the distal end thereof, to the gasket.

10. The injection device as defined in 9 above, wherein the connection of the piston rod and the gasket is made by screw engagement between a female thread formed in the rear part of the gasket and a male thread formed around the distal end of the piston rod.

11. The injection device as defined in 9 or 10 above, wherein the syringe, at the proximal end thereof, has increased thickness of the wall and enlarged outer diameter, the inner diameter of the barrel portion of the syringe holder is smaller at the proximal end thereof than said outer diameter, and the proximal end of the barrel portion of the syringe holder blocks the proximal end of the syringe from entering the syringe holder.

12. The injection device as defined in one of 9 to 11 above, wherein the inner surface of the bore in the proximal end cap contacts the outer surface of the piston rod.

13. The injection device as defined in one of 9 to 12 above, wherein the piston rod is provided with a projection on the outer surface thereof, and the outer diameter of the piston rod, when including the tip of the projection, is greater than the inner diameter of the bore in the proximal end cap, and wherein the bore is so shaped that it allows the projection to pass forwardly from behind, getting over the bore, but causes greater resistance to the passage of the piston rod in the reverse direction.

14. The injection device as defined in 13 above, wherein the front face of the projection is backwardly inclined relative to the outer surface of the piston rod, and the pitch of inclination of the rear face of the projection is steeper relative to the outer surface of the piston rod than the front face of the projection.

According to the present invention as defined above, as a syringe, with a cap being kept attached to the luer tip, can be inserted into the holder, it is now possible to insert a syringe into the holder after the syringe is filled with an injectable liquid. Therefore, it is only caps, syringes and gaskets that must be brought in an aseptic room. And insertion of syringes into the holders may be carried out in a less strict circumstance, after the syringes are filled with an injectable liquid and taken out of the aseptic room. Thus, it is now possible to reduce the number of the parts that should be sterilized, and it is no more necessary to assemble, prior to a sterilization process, a part for achieving luer locking and a syringe, nor to assemble separately sterilized parts prior to filling in an aseptic room. Thus, the present invention greatly improves the production efficiency in the whole flow of the processes, from preparation works before sterilization and sterilization to filling with an injectable liquid and to assembly process.

Furthermore, according to the present invention with the features defined in one of paragraphs 6 to 8 above, even when connection has to be made to a counterpart connector device which is not adapted to the luer lock system, the distal portion of the holder can be detached and removed from the proximal portion of the holder, to expose the male luer of the syringe while the cap being kept attached to the luer tip of the syringe. Therefore, the injection device can be converted from one that is adapted to the luer lock system to one adapted to the simple luer fitting system, and, since there is no risk of contamination or fracture of the tip of the syringe when this conversion is effected, it enables to achieve safe and unfailing connection.

EXPLANATION OF THE SIGNS

Figure 1:
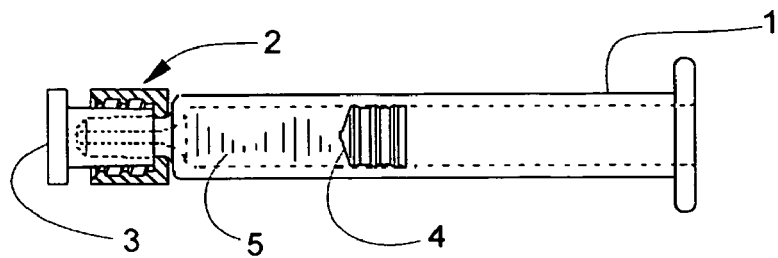
FIG. 1 is a side view of a conventional luer lock syringe.
Figure 2:
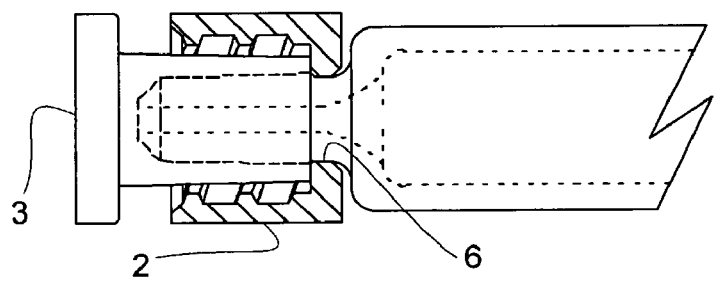
FIG. 2 is an enlarged view of the distal part of a conventional luer lock syringe.

1=syringe, 2=female-threaded sleeve, 3=cap, 4=gasket, 5=injectable liquid, 6=squeezed portion, 11=syringe, 12=male luer, 13=cap, 14=gasket, 15=injectable liquid, 21=barrel portion, 23=female-threaded sleeve, 24=rib, 25=finger rest, 26=ridge, 27=proximal end cap, 29=male thread, 31=piston rod, 33=male thread, 35=projection, 37=female thread, 40=outer edge of distal end, 42=face of annular upthrust, 44=proximal end of syringe, 45=female thread, 47=finger grip portion, 50=distal portion, 52=proximal portion, 55=face of annular upthrust

DETAILED DESCRIPTION OF THE INVENTION

The syringe used in the present invention is of a cylindrical shape having a simple luer-type tip (i.e., having a male luer at the distal end of the syringe). Syringes which are filled with an injectable liquid and sealed with a cap fitted at their tip and a gasket in their cylindrical body are widely used, for injection, esp. of a small volume of an injectable liquid. The length, the internal diameter and the dimensions of the stopper means, which is to abut on the outer edge of the distal end of the syringe, of the syringe holder of the present invention may be determined in accordance with the specification of dimensions of each of a varying syringes.

The dimensions of the female thread for luer lock syringes are defined by the International Standard (ISO594-2: Conical fittings with a 6% (Luer) taper for syringes, needles and certain other medical equipment—Part 2: Lock fittings): the inner diameter of the female thread is 7.2 (upper tolerance 0 mm, lower tolerance: −0.2 mm), and the outer diameter of the female thread is 8 (upper tolerance: 0 mm, lower tolerance: −0.1 mm). It is preferred that the dimensions of the female-threaded sleeve in the present invention is in conformity to this specification. In the present invention, in order that the cap attached to the tip of the syringe can be moved within the syringe holder, either forwardly from behind to the inside of the female-threaded sleeve or backwardly from inside of the female-threaded sleeve to the inside of the barrel of the syringe holder, it is preferred that the outer diameter of the cap at the thickest part of it is not more than 7 mm. However, as the cap is made of an elastic material such as rubber as with conventional caps so that it can seal the male luer of the syringe, it can be deformed to some degree. Therefore, as far as the cap can be deformed and pass through with ease, it is may have a diameter somewhat greater than 7 mm.

The stopper means provided in the syringe holder includes of a surface which is inwardly upthrust and abuts on the outer edge of the distal end of the syringe in order to prevent the syringe from forwardly advancing beyond it. Examples which provide such a surface include an inward projection, two or more inward projections arranged along a common circumference, an annular projection, tapered inner wall, and the like. However, the shape and dimensions of the stopper means may be determined as desired insofar as it blocks the syringe without fail from advancing while allowing the cap to pass through. Considering convenience in production, the stopper means is preferably an annular inward upthrust. It is convenient and thus further preferable that every cap that can pass through the female-threaded sleeve can also pass through the stopper means. A method to guarantee this is to restrict the dimensions of the stopper means so that it does not intrude into the inside of a cylindrical surface which fits the top of the thread of the female-threaded sleeve. Considering production of a syringe holder, a most convenient shape for this is one in which the stopper means is formed as an annular upthrust which is level with the top of the thread of the female-threaded sleeve.

The proximal end cap of the syringe holder may be of any configuration insofar as it can constrain, and thereby prevent backward movement of, the edge of the proximal end of the syringe which is exposed at the proximal end of the barrel portion of the syringe holder containing the syringe. Fixation of the proximal end cap may be done by, e.g., forming a recess (or a projection) in the outer surface of the barrel portion near its proximal end and further forming a projection (or a recess) in the proximal end cap so that the barrel portion and the proximal end cap engage with each other in a snap fit manner, or, alternatively, by providing each of them a thread so that they are screw-fixed with each other. Though the inner diameter of the bore in the proximal end cap for allowing the piston rod to pass through may be substantially greater than the outer diameter of the piston rod, it is preferably of nearly the same size with the outer diameter of the piston rod so that it contact the outer surface of the piston rod, since such a configuration stabilizes the axis of the piston rod.

The finger rest of the syringe holder may be of any configuration insofar as it is a structure expanding from the outer surface of the syringe holder relatively closer to the proximal end of its barrel portion (than to its distal end) so that it allows fingers to be placed on it when holding the syringe holder. For example, it may be, but not is limited to, a circular plate-like projection surrounding the whole outer circumference, or plate- or rod-like projections extending in the opposite directions from each other, and the like.

The barrel portion of the syringe holder may either be formed as an one body or consist of two or more portions assembled with each other which can be disassembles when desired, for it is enough that the barrel portion can hold a syringe inserted in it. Even if a counterpart connector device to which the syringe is to be connected does not accept, due to its structure, syringes of the luer lock system, a barrel portion composed of a distal portion and a proximal portion which are separably assembled by screw engagement, snap fitting or the like, would allow the syringe to be used for simple luer fitting, by removing without difficulty the distal portion from the proximal portion of the barrel portion. Upon this, as the distal portion of the barrel portion of the syringe holder can be removed, while the cap is kept attached to the luer tip of the syringe, there is no risk of contamination or fracture of the syringe tip. With this regard, the distal portion is connected with the proximal portion preferably at a site forward of the finger rest, for it is desirable that the finger rest is left with the proximal portion when the distal portion has been removed.

The present invention also provides an injection device which is composed of a syringe holder holding within itself a syringe having a cap attached to the tip and a gasket inserted therewithin, and a piston rod connected to the gasket. The piston rod may be connected to the gasket in any manner as desired. In a conventional manner, a male thread formed around the distal end of a piston rod is inserted into a female thread formed in the rear part of the gasket, and turned to effect screw engagement with it. The same manner of connection is preferably employed in the present invention.

If the barrel portion of the syringe holder is composed of a distal portion and a proximal portion which are separably connected with each other, it is preferable, in preparation for the holder being used with its distal portion removed, that the proximal portion of the barrel portion of the syringe holder is so made that the it can hold the syringe in concert only with the proximal end cap. To do this, the inner diameter of barrel portion of the syringe holder may be made to be nearly identical to the outer diameter of the syringe so that the inner surface of the barrel portion of the syringe holder may substantially closely fit the outer surface of the syringe. A syringe to be inserted in the syringe holder, in general, is of a small size and made of glass, and, from the necessity of increasing the strength of the brittle end of the glass, has increased thickness of the wall at its proximal end, thereby having an enlarged outer diameter there compared with the diameter at the other part. Therefore, by making the inner diameter of barrel portion of the syringe holder to be nearly the same as the outer diameter of the syringe except for the proximal end, so that the outer diameter of the syringe may substantially closely fit the inner surface of the barrel portion of the syringe holder, the inner diameter of barrel portion of the syringe holder is made smaller than the outer diameter of the proximal end of the syringe. By this configuration, the proximal end of the syringe is prevented from entering the inside of the barrel portion of the syringe holder. The syringe, whose forward movement is thus prevented, is also prevented by the proximal end cap from moving backward, and therefore held at a fixed position relative to the syringe holder. It is permissible, however, that the inner diameter of the barrel portion is somewhat greater than the outer diameter of the syringe except for the proximal end, since it is sufficient that the outer diameter of the syringe at its proximal end is greater than the inner diameter of the barrel portion of the syringe holder at its proximal end.

Though not essential, it is preferable that measures are taken to prevent the piston rod from being inadvertently pulled back too much even when the piston rod must be pulled back, e.g., in a flashback procedure in injection to confirm whether access has been gained to a blood vessel or for preparation of mix injection. To do this, the piston rod may be provided with a projection of such a shape that does not hider insertion of the piston rod in the assembly process but offer substantial resistance to the user when the piston rod is pulled backward, thus giving a warning to the user who is excessively pulling the piston rod. The height of such a projection is such that the outer diameter of the piston rod, including the tip of the projection, is greater than the inner diameter of the bore in the proximal end cap, but that insertion of the piston rod in the forward direction is permitted in the process of assembly of the injection device. Herein, "the outer diameter of the piston rod, including the tip of the projection" means the diameter of a circle which circumscribes the transverse section of the piston rod cut through the tip of the projection. Even when the tip of the projection interferes with the edge of the bore in the proximal end cap, if it is only slight interference and/or if the cap is formed of a flexible material such as a soft plastic, the projection can relatively easily advance beyond the edge of the bore owing to the elasticity of the material. With regard to their shape, the projection and the edge of the bore are preferably such that the resistance to the forward movement of the projection passing by the edge of the bore is relatively smaller, while the resistance to the backward movement is relatively greater. Any of specific shapes that would exhibit this feature may be designed as desired by those skilled in the art. A first example of preferred shapes is one in which the front face of the projection is backwardly inclined relative to the outer surface of the piston rod, and the pitch of inclination of the rear face of the projection relative to the outer surface of the piston rod is steeper, for example almost vertically elevated or even inclined backward. A second example of preferred shapes is one in which the slopes of the front and rear faces of the projection are comparable to each other but the edge of the bore in the proximal end cap, in its longitudinal cross section, is of the shape of a funnel with its inner diameter expanding backwardly. Though any of these shapes may be adopted, or the both may be adopted in combination, the shape of the projection described as the first example as above is conveniently adopted and particularly preferred.

Though there is no specific limitation regarding the materials of which the syringe holder of the present invention is to be made, it is preferred that the barrel portion, the female-threaded sleeve and the finger rest are formed of a rigid plastic and the proximal end cap of a relatively soft plastic. Such use of a relatively soft plastic, because of its flexibility, serves to keep the strength of the pressure on the proximal end of the syringe within a proper range and thereby to stabilize holding of the syringe, and moreover, if the aforementioned projection is provided on the piston rod, serves to enhance the aforementioned effect of its inclined faces. It is particularly preferred that the barrel portion of the syringe holder is formed of a transparent material (polycarbonate and the like) so that a syringe inserted in it may be visible from outside through the syringe holder.

EXAMPLES

The present invention will now be described in further detail below with reference to typical examples. However, it is not intended that the present invention be restricted to the examples.

Example 1

Figure 3:
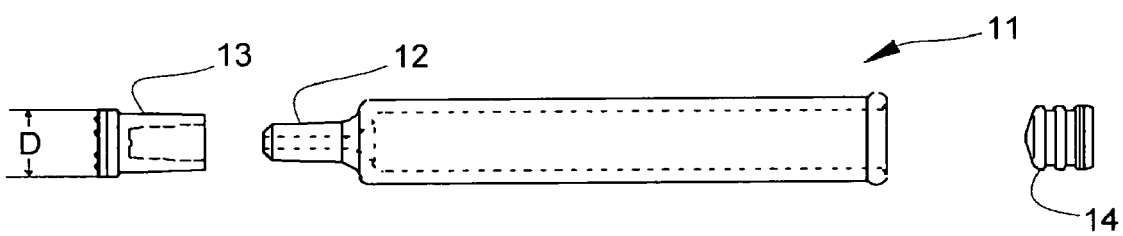
FIG. 3 is a side view illustrating a syringe, a cap and a gasket.
Figure 4:
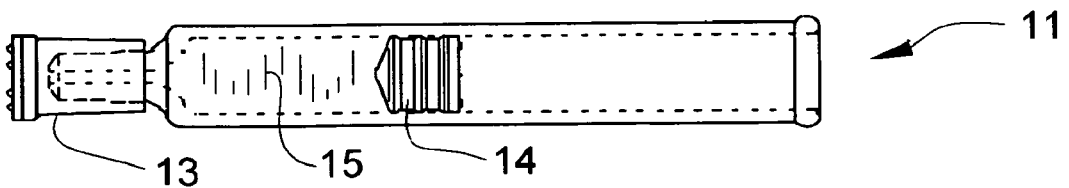
FIG. 4 is a side view illustrating a syringe, a cap and a gasket after assembled.

FIG. 3 illustrates a side view of a cylindrical glass syringe 11, a synthetic rubber cap 13 and a synthetic rubber gasket 14, which are used in the present invention. Numeral 12 indicates the male luer at the tip of the syringe. Regarding the cap 13, "D" indicates the maximum outer diameter, which is 7 mm in this example. FIG. 4 illustrates the parts shown in FIG. 3 which has been assembled. Numeral 15 indicates an injection liquid which has filled the syringe.

Figure 5:
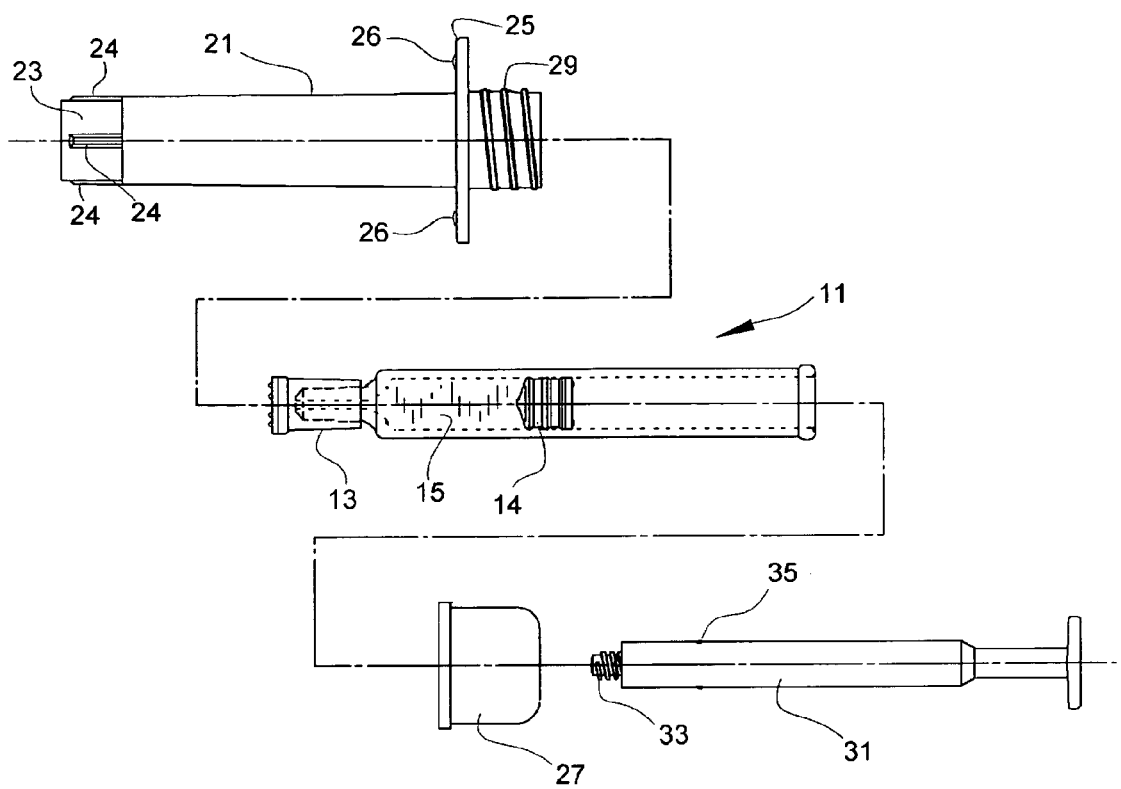
FIG. 5 is a assembly drawing illustrating a syringe holder before assembly, and indicating the positional relationship between the syringe and the syringe holder.

FIG. 5 is an assembly drawing illustrating a syringe holder before assembly and indicating the positional relationship of the parts when the syringe 11 filled with the injection liquid 15 is inserted into the syringe holder of the present invention and then a piston rod is attached to assemble the injection device. In the figure, numeral 21 indicates a barrel portion which constitutes a part of the syringe holder and is formed of polycarbonate. At the distal end of the barrel portion 21 extends a female-threaded sleeve 23, which is integrally molded with the barrel portion 21, and numeral 24 indicates ribs reinforcing the female-threaded sleeve. From the outer surface of the barrel portion 21, at a position relatively closer to its proximal end (than to its distal end), projects a finger rest 25 which is integrally molded with the barrel portion 21. Two parallel ridges 26 are formed on the front surface of the finger rest 25 for the purpose of preventing slippage. The syringe 11, with the cap 13 kept attached, is inserted through the proximal end of the barrel portion 21, until the male luer at the distal end of the syringe is received in the female-threaded sleeve 23 and the outer edge of the distal end of the syringe 11 abuts on the inner surface of the distal end of the barrel portion 21, and then a proximal end cap 27 is attached to cover the proximal end of the barrel portion 21. The proximal end cap 27, which is provided with a female thread on its internal surface, is fixed over the proximal end of the barrel portion 21, while exerting pressure on the proximal end of the syringe 11 in the forward direction, by screwing the female thread over a male thread formed on the outer surface of the barrel portion 21 at or close to its proximal end. Thus, the syringe 11 is fixed in place, with back and forth movement of it being no more allowed. In the center of the proximal end cap 27 is defined a through bore, through which the piston rod 31 is inserted. A male thread 33 is formed around the distal end of the piston rod 31. The male thread 33 is screw-fixed to a female thread (not shown) in the rear part of the gasket 14 within the syringe by applying the former to the latter and rotating the piston rod 31. In the figure, numeral 35 indicates projections, which are two in number and placed on the opposite side of the outer surface of the piston rod 31. Each of the projections 35, in the longitudinal cross section, has a front face which is backwardly inclined to form a slope at an angle of 30° with the outer surface of the piston rod 31, while a rear face of the projection is vertical relative to the outer surface of the piston rod 31.

Figure 6:
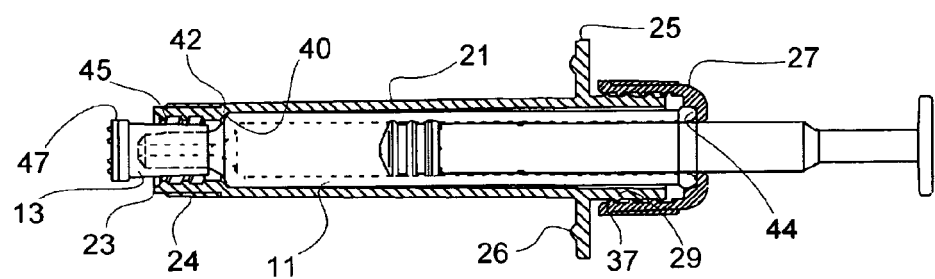
FIG. 6 is a side view illustrating the assembled injection device, with a portion shown in a cross section.

FIG. 6 illustrates a side view of the assembled injection device, with a portion (syringe holder) shown in a cross section. As seen in the figure, the syringe 11 abut, at the outer edge 40 of its distal end, on an annular inward upthrust 42 (stopper) formed at the distal end of the barrel portion 21 of the syringe holder, and cannot move forward from the position shown in the figure. The proximal end 44 of the syringe 11 is pressed forward, by screw-fixing the female thread 37 formed on the inner surface of the proximal end cap 27 around the male thread 29 formed on the outer surface near the proximal end barrel portion 21. The inner diameter of the female thread 45 formed on the inside of the female-threaded sleeve 23 is 7 mm, as with the outer diameter of a finger grip portion 47 of the cap 13, at which the outer diameter is greatest. And the height of the top of the annular inward upthrust 42(stopper) formed at the distal end of the barrel portion 21 of the syringe holder is level with the height of the top of the female thread 45. Thereby, the cap 13 can pass through without difficulty from the barrel portion 21 of the syringe holder to the inside of the female-threaded sleeve 23, when the injection device is assembled.

Example 2

Figure 7:
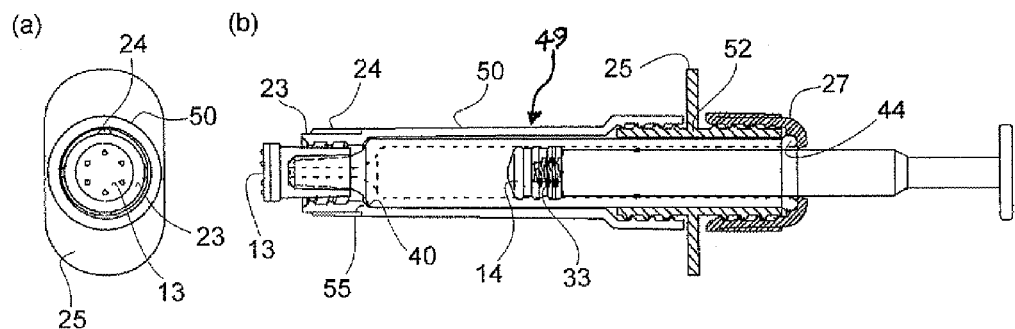
FIG. 7 is a side view illustrating the assembled injection device of Example 2, with a portion shown in a cross section.
Figure 8:
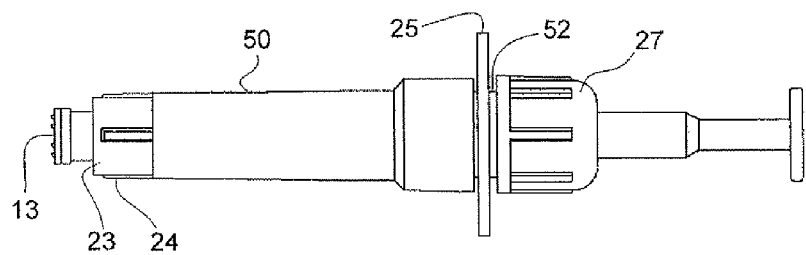
FIG. 8 is a side view of the assembled injection device of Example 2.
Figure 9:
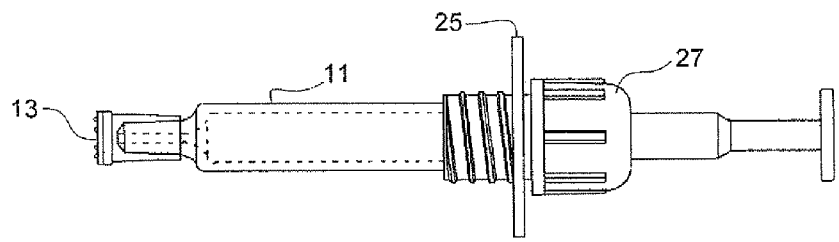
FIG. 9 is a side view illustrating the injection device of Example 2 after the distal portion has been pulled off.

FIG. 7 illustrates an end view of the distal end (a) and a side view (b), of the assembled injection device of another example, with a portion shown in a cross section. In the figure, the syringe 11, cap 13, gasket 14 and piston rod 31 are identical to those in Example 1. This example differs from Example 1 in that the barrel portion 49 of the syringe holder here is composed of a distal portion 50 and a proximal portion 52. The finger rest 25 is integrally molded with the proximal portion 52 of the barrel portion, and the distal portion 50 of the barrel portion is screw-fixed, forward of the finger rest 25, on the proximal portion 52 of the barrel portion. While the wall of the syringe 11 has increased thickness at its proximal end 44 and, as a result, enlarged outer diameter there, the inner diameter of the proximal portion 52 of the barrel portion is smaller than the outer diameter of the distal end of the syringe. Therefore, the syringe 11 cannot forwardly advance from the position shown in the figure. Thus, the syringe 11 is held there sandwiched, at the edge of its proximal end, by the proximal portion 52 of the barrel portion of the syringe holder and the proximal end cap 27. At the same time, the outer edge 40 of the distal end of the syringe 11, as in Example 1, abuts on the face of the annular inward upthrust 55 formed at the distal end of the distal portion 50 of the barrel portion of the syringe holder. FIG. 8 illustrates a side view of the present example, in which the syringe which is seen through the barrel portion of the syringe holder is not shown, and FIG. 9 illustrates a side view of the device shown in FIG. 8 after the distal portion 50 of the barrel portion has been pulled off, while the cap 11 is kept attached to the syringe 11. Thus, the injection device of the present example can be connected not only to luer lock-type connector devices but also to connector devices that are adapted only to a simple luer fitting-type male luer, easily and without a risk of contaminating the tip of the syringe.

INDUSTRIAL APPLICABILITY

The present invention is useful as a luer lock-type injection device and a syringe holder as a part of it that serve to improve the complexity of the process of sterilization, thereby reducing the cost and improving production efficiency. A type of the present invention is further useful as an injection device that allows its easy and safe connection, at a clinical spot, even to a counterpart connector device that cannot be connected to a luer lock-type injection device.

What is claimed is:

1. A syringe holder for holding an inserted cylindrical syringe, with a cap attached to a male luer provided at the distal end thereof, comprising a generally cylindrical barrel portion having an open distal end and an open proximal end, and a finger rest projecting in the lateral direction from the outer surface of the barrel portion at a position relatively closer to the proximal end of the barrel portion,
wherein a female-threaded sleeve is provided which extends forwardly from the distal end of the barrel portion, the female-threaded sleeve being provided with a thread designed to surround the male luer provided at the distal end of the syringe and the cap attached to the male luer, and
wherein a proximal end cap is provided, at the proximal end of the barrel portion, the proximal end cap being designed to cover the proximal end of the barrel portion and to abut on the outer edge of the proximal end of the syringe to block backward movement of the syringe, and the proximal end cap having a bore through which to pass a piston rod that is to be connected to a gasket in the syringe and
wherein the barrel portion consists of a distal portion and a proximal portion which are separately connected with each other at a site forward of the finger rest in a manner that rear part of the distal portion covers the front part of the proximal portion,
wherein a stopper is provided at the inner surface of the barrel portion at the distal end thereof, the stopper being designed to abut on the outer edge of the distal end of the syringe to block forward movement of the syringe,
wherein the stopper is of a shape and dimensions that do not block the passage of the cap upon insertion of the syringe into the syringe holder, and the distal portion of the syringe holder is removable from the proximal portion of the syringe holder with the cap being kept attached to the luer tip of the syringe, and
wherein the stopper does not intrude into the inside of a cylindrical surface defined by the top of the thread of the female-threaded sleeve.

2. The syringe holder of claim 1, wherein the stopper consists of an inward upthrust from the inner surface of the barrel portion.

3. The syringe holder of claim 1, wherein the proximal end cap is attached to the proximal end of the barrel portion by screw engagement between the outer surface of the barrel portion at or close to the proximal end thereof and the inner surface of the proximal end cap.

4. An injection device comprising a cylindrical syringe having a gasket inserted therewithin and a cap attached to a male luer provided at the distal end thereof, the syringe holder of claim 1 holding the syringe therein, and a piston rod passing through the bore in the proximal end cap for the syringe holder and connected, at the distal end thereof, to the gasket.

5. The injection device of claim 4, wherein the connection of the piston rod and the gasket is made by screw engagement between, a female thread formed in the rear part of the gasket and a male thread formed around the distal end of the piston rod.

6. The injection device of claim 4, wherein the syringe, at the proximal end thereof, has increased thickness of the wall and enlarged outer diameter, the inner diameter of the barrel portion of the syringe holder is smaller at the proximal end thereof than said outer diameter, and the proximal end of the barrel portion of the syringe holder blocks the proximal end of the syringe from entering the syringe holder.

7. The injection device of claim 4, wherein the inner surface of the bore in the proximal end cap contacts the outer surface of the piston rod.

8. The injection device of claim 4, wherein the piston rod is provided with a projection on the outer surface thereof, and the outer diameter of the piston rod, when including the tip of the projection, is greater than the inner diameter of the bore in the proximal end cap, and wherein the bore is so shaped that it allows the projection to pass forwardly from behind, getting over the bore, but causes greater resistance to the passage of the piston rod in the reverse direction.

9. The injection device of claims 8, wherein the front face of the projection is backwardly inclined relative to the outer surface of the piston rod, and the pitch of inclination of the rear face of the projection is steeper relative to the outer surface of the piston rod than the front face of the projection.

10. A syringe holder for holding an inserted cylindrical syringe, with a cap attached to a male luer provided at the distal end thereof, comprising a generally cylindrical barrel portion having an open distal end and an open proximal end, and a finger rest projecting in the lateral direction from the outer surface of the barrel portion at a position relatively closer to the proximal end of the barrel portion,
wherein a female-threaded sleeve is provided which extends forwardly from the distal end of the barrel portion, the female-threaded sleeve being provided with a thread designed to surround the male luer provided at the distal end of the syringe and the cap attached to the male luer, and
wherein a proximal end cap is provided, at the proximal end of the barrel portion, the proximal end cap being designed to cover the proximal end of the barrel portion and to abut on the outer edge of the proximal end of the syringe to block backward movement of the syringe, and the proximal end cap having a bore through which to pass a piston rod that is to be connected to a gasket in the syringe and
wherein the barrel portion consists of a distal portion and a proximal portion which are separately connected with each other at a site forward of the finger rest by screw engagement between a female screw formed on the inner surface of the rear part of the distal portion and a male screw formed on the outer surface of the front part of the proximal portion, wherein a stopper is provided at the inner surface of the barrel portion at the distal end thereof, the stopper being designed to abut on the outer edge of the distal end of the syringe to block forward movement of the syringe, wherein the stopper is of a shape and dimensions that do not block the passage of the cap upon insertion of the syringe into the syringe holder, and the distal portion of the syringe holder is removable from the proximal portion of the syringe holder with the cap being kept attached to the luer tip of the syringe, and wherein the stopper does not intrude into the inside of a cylindrical surface defined by the top of the thread of the female-threaded sleeve.

11. The syringe holder of claim 10, wherein the stopper consists of an inward upthrust from the inner surface of the barrel portion.

12. The syringe holder of claim 10, wherein the proximal end cap is attached to the proximal end of the barrel portion by screw engagement between the outer surface of the barrel portion at or close to the proximal end thereof and the inner surface of the proximal end cap.

* * * * *